US005516960A

United States Patent [19]
Robinson

[11] Patent Number: 5,516,960
[45] Date of Patent: May 14, 1996

[54] PROCESS FOR PRODUCING HYDROCARBON FUELS

[75] Inventor: J. Michael Robinson, Odessa, Tex.

[73] Assignee: Board of Regents, The University of Texas System, Austin, Tex.

[21] Appl. No.: 285,635

[22] Filed: Aug. 2, 1994

[51] Int. Cl.$^6$ ..................................................... C07C 1/00
[52] U.S. Cl. .......................... 585/639; 585/310; 585/324; 585/611; 585/733; 570/101; 568/671
[58] Field of Search .................................... 585/469, 611, 585/640, 733, 310, 324, 639; 570/101, 181; 568/671

[56] References Cited

U.S. PATENT DOCUMENTS

| 3,914,340 | 10/1975 | Gordon | 568/659 |
| 4,401,823 | 10/1984 | Arena | 549/356 |
| 4,476,331 | 10/1984 | Dubeck | 568/861 |

OTHER PUBLICATIONS

Appell, H. R. et al., "Conversion of Cellulosic Wastes to Oil", Report of Investigations 8013, U.S. Bureau of Mines (1975).
Appell, H. R. et al., "Converting Organic Wastes to Oil", Report of Investigations 7560, U.S. Bureau of Mines (1971).
Cooper, D. et al., "A Low Pressure–Low Temperature Process for the Conversion of Wood to Liquid Fuels and chemicals Using Hydrogen Iodide", Canadian Bioenergy Research and Development Seminar [Proc.] 5th, pp. 455–459 (1984).
Creighton, H. Jermain, "The Electrochemical Reduction of Sugars", Trans. Electrochem. Soc. 75:289–307 (1939).
Goldstein, Irving S., "Potential for Converting Wood into Plastics", Science 189(4206):8347–852 (1975).
Mitchell, Herschel K. et al., "A Study of Reduction with Hydriodic Acid: Use in Micro Determinations of Hydroyxl Groups", J. Am. Chem. Soc. 60:2723–2726 (1938).
Nakamura, Yoshio, "Reduction of polyalcohols", Chemical Abstracts 91:600 abstract 19910X, (1979).
Sarkanen, Kyosti V., "Renewable Resources for the Production of Fuels and Chemicals", Science 191:773–776 (1976).
Sharkov, V. I., "Production of Polyhydric Alcohols from Wood Polysaccharides", Angewandte Chemie 2(8):405–492 (1963).
Soltes, E. J. et al., "Of Biomass, Pyrolysis and Liquids Thereform", in Pyrolysis Oils from Biomass, (Soltes, E. J. and Milne, T. A. eds.) ACS Symposium Series 376, Chapter 1, American Chemical Society (1988).
Vincent, C. "Chimie Organique–Sur la sorbite", Compt. Rend. 109:677 (1890): non–English language document.
Willstatter, et al., "Reduction of lignin and of carbohydrates with hydriodic acid and phosphorus", Chemical Abstracts 17:982–983 (1923).
"Chemicals from wood are economical now", Technology Report, Chem. & Eng. News, pp. 4–5, Dec. 6, 1976.
"IGT weighs potential of fuels from biomass", Technology Report, Chem. & Eng. News, pp. 24–26, Feb. 23, 1976.

Primary Examiner—Ponnathapura Achutamurthy
Attorney, Agent, or Firm—Michael A. Sanzo; Vinson & Elkins

[57] ABSTRACT

The present invention is directed to method for chemically converting polyhydric alcohols to a mixture of hydrocarbons and halocarbons. The invention is also directed to a process for converting cellulose or hemicellulose to hydrocarbon fuels.

15 Claims, 2 Drawing Sheets

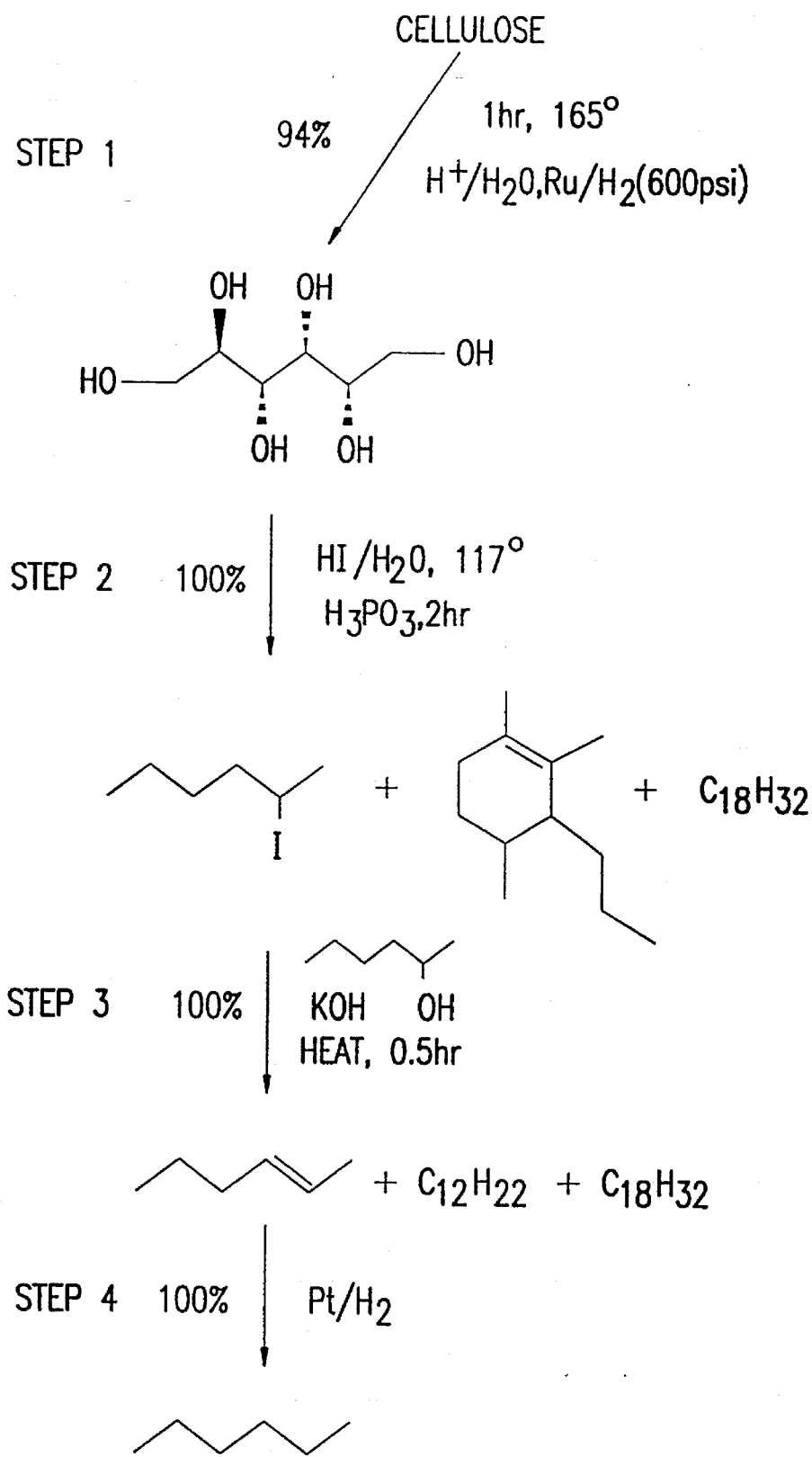
CHART I

PROCESS FOR PRODUCING HYDROCARBON FUELS

FIELD OF THE INVENTION

The invention is in the field of organic chemistry as related to the chemical production of hydrocarbon fuels.

BACKGROUND OF THE INVENTION

I. Conversion of Biomass to Chemical Feedstocks and Hydrocarbon Fuels

Vegetation biomass (hereinafter "biomass") includes all of the plants, crops and trees found within a given habitat. Cellulose and hemicellulose, the chief components of biomass, are renewable resources of energy and chemical feedstocks (Technology Report, *Chem. & Eng. News*, Feb. 23, 1976, pp. 24; Goldstein, I. S., *Science* 189:847 (1975)). Although biomass may be converted into gas or liquid fuels by fermentation or by pyrolysis at high temperature and pressure, these processes have significant drawbacks.

Fermentations suffer from poor efficiency. Processes resulting in the production of methane conserve only about 60% of the fixed energy of the biomass starting material (Technology Report, *Chem. & Eng. News*, pp. 24, Feb. 23, 1976). Fermentations leading to the production of ethanol are even less efficient (50% cellulose in wood×50% conversion to glucose×95% yield of ethanol×67% carbon recovery=16% yield) (Goldstein, I. S., *Chem. & Eng. News*, pp. 4, Dec. 6, 1976). The theoretical limit of energy conversion by ethanol production is 67% due to the loss of one/third of the available carbon as carbon dioxide gas.

Pyrolyric processes also tend to be inefficient. For example, the pyrolytic conversion of biomass to water gas ($CO_2+H_2 \rightleftarrows CO+H_2O$) results in a large loss of the intrinsic caloric value of the starting material due to the loss of 30–50% of carbon as carbon dioxide (Goldstein, I. S., *Science* 189:847 (1975)). Pyrochemical processes which convert biomass into crude fuel oil lose carbon as char and gases (Appell, H. R., et. al., Bureau of Mines R.I. #7560, U.S. Department of the Interior, Washington, D.C., (1971); Appell, H. R., et. al., Bureau of Mines R.I. #8013, U.S. Department of the Interior, Washington, D.C., (1975)). As a result, such processes typically result in only about an 80% conversion of biomass carbon. Because of these and other factors, quantitative yields of suitable liquid fuels have not been obtained using either fermentations or pyrolytic reactions.

Pyrolytic processes require dry feedstocks (Soltes, E. J., ACS Symposium Series #376, chapter 1, (Soltes, E. J. and Milne, T. A., eds.) American Chemical Society, Washington, D.C., (1988)). As a result, it is impractical to use such processes with those sources of biomass that have a high moisture content. For example, it would not be practical to use aquatic plants in most pyrolytic reactions.

There is an increasing need for a variety of fuels (especially conventional liquid fuels) and for new sources of conventional chemicals and chemical feedstocks (Goldstein, I. S., pp. 4, *Chem. & Eng. News*, Dec. 6, 1976; Sarkaren, K. V., *Science* 191:773 (1976)). Processes capable of producing such products in high efficiency from readily available sources of biomass would clearly be of great value.

II. Conversion of Polyhydric Alcohols to Iodoalkanes and Hydrocarbons

The cellulose and hemicellulose components of biomas, could potentially provide the starting material for a chemical pathway for the production of hydrocarbon fuels and chemical feedstocks. Efficient methods for converting these components into polyhydric alcohols have been reported in the literature (see Sharkov, V. I., *Angew. Chem. I.E.E.* 2:405 (1963); see also Creighton, H. J., *Trans. Electrochem. Soc.* 75:289 (1939)). Although methods are available for reacting polyhydric alcohols with hydriodic acid to produce iodoalkanes these methods have been inefficient either because of poor rates of conversion or because they have required the use of massive quantities of reagents.

Historically, the chemical conversion of reactants to 2-iodohexane has been used as a means of proving the structure of sugars. Typically, polyhydric alcohols such as sorbitol are reacted with a very large excess of hydriodic acid (e.g. at an 85/1 mole ratio), in a sealed glass capillary, at 135° C. and at low pressure to give 2-iodohexane (Mitchell, H. K. et. al., *J. Amer. Chem. Soc.* 60:2723 (1938)). Under these conditions, five hydroxy groups are reduced, and one hydroxy group undergoes substitution. The reaction is conducted on an analytical scale, and a titration is then performed to determine the amount of iodine liberated by the reduction reaction. This reaction is the basis for Zeisel's test for alkoxy groups on sugars.

When the Zeisel type reaction is performed on a larger scale, with a lower ratio of HI to polyhydric alcohol, only small amounts of iodoalkane are produced. The reaction stops due to mechanical problems associated with phase separation caused by the presence of both a large amount of iodine and, perhaps, polyiodo intermediates. Apparently, these by-products are poorly soluble in a simple aqueous system.

A Japanese patent describes the reduction of sorbitol with HI, but 2-iodohexane was recovered in only a 22% yield (Nakamura, Y., Jap. Pat. No. 78,144,506, (1978); *Chem. Abstr.* 91:19910x(1979)). Nakamura used a 1/1 mole ratio of reactants in an acetic acid solvent containing $H_2$ and chloroplatinate. The reaction was performed at 110° C. and 710 psi for 2.5 hours.

An article published in 1890 reported that sorbitol reacts with aqueous HI and red phosphorous to produce 2-iodohexane in 95% yield in a reaction performed on a 0.3 mole scale (Vincent, C., *Compt. Rend* 109:677 (1890); *Beil.* 59:533 (1918)). By-product $I_2$ is consumed by the phosphorous during the reaction. This result demonstrates that sorbitol can be converted to iodohexane in high yield if $I_2$ reacts quickly enough so that it does not interfere with the reduction reaction. Unfortunately, the solid red phosphorous creates mechanical problems in the reaction due to the presence of heterogeneous phases. Also, the rate of $I_2$ conversion is limited by the surface area of the solid particles.

Another early reference reported that, when sorbitol and mannitol are reacted with HI and red phosphorous in a sealed tube at 250° C. for 5 hours, small amounts of high molecular weight hydrocarbons are produced in addition to iodohexane (Willstatter, R., et. al., *Chemische Ber.* 55b:2637 (1922); *Chem. Abstr.* 17:982 (1923)). These hydrocarbons are similar in composition to those produced in the same way from cellulose, lignin, or other carbohydrates.

Ideally, the efficient conversion of polyhydric alcohols to iodoalkanes and hydrocarbons would be accomplished by homogeneous chemical agents that rapidly reduce $I_2$. This would provide a key reaction in pathways for the conversion of sorbitol or xylitol derived from biomass into hydrocarbon fuels and chemical feedstocks.

SUMMARY

The present invention is directed to a method for converting polyhydric alcohols, particularly those derived from biomass, into hydrocarbons and iodoalkanes. The liquid hydrocarbons may be used directly as fuels. The iodoalkanes may either themselves be converted into hydrocarbons or oxygenated fuels or they may be used as feedstocks in other chemical processes. The conversion method disclosed herein comprises reacting an aqueous mixture containing: one or more polyhydric alcohols; hydriodic acid; and a liquid phase phosphorous-containing reducing agent.

By controlling the concentration and type of reagents used in the method, the hydrocarbon products obtained can be monomeric with respect to the polyhydric alcohol starting material or an oligomer thereof. Depending upon the product desired, favorable results may be obtained using either phosphorous acid or hypophosphorous acid as the reducing agent and by carefully controlling the extent to which reagents are diluted with water. The method can be used for any polyhydric alcohol, including sorbitol, xylitol, mannitol, arabitol or dulcitol and most particularly with those polyhydric alcohols derived from biomass.

The present invention is also directed to a multistep process for converting cellulose, hemicellulose, or a mixture of cellulose and hemicellulose into hydrocarbon fuels and chemical feedstocks. In its broadest aspect, this process consists of two steps: 1) the depolymerization of cellulose or hemicellulose into sorbitol or xylitol; and 2) the chemical conversion of the sorbitol or xylitol products into a mixture of iodoalkanes and hydrocarbons by the method described above. In a preferred third step, the iodoalkanes contained in the hydrocarbon mixture produced in step 2 are convened into alkenes. This reaction ensures that hydrocarbon fuels do not contain any halogens that would be corrosive upon combustion. The alkenes produced from iodoalkanes may be isolated or, alternatively, they may be reduced to alkanes. Iodoalkanes may also be removed from the hydrocarbon mixture produced in step 2 by distillation and then separately converted into pure alkenes or alkanes.

The first step of the process, i.e. the depolymerization of cellulose or hemicellulose, may be accomplished by means of a reaction in aqueous solution containing polymer, $H_3PO_4$ (about 0.7%) and a ruthenium catalyst (about 0.5%). The reaction is performed at a temperature of about 165° C. and at an $H_2$ pressure of about 600 psi. Sharkov, V. I., *Angew. Chem. I.E.E.* 2:405 (1963)).

In the third step of the process, the halocarbons found within the mixture of products produced by step 2 are converted to alkenes. Preferably, the conversion is accomplished by an elimination reaction using potassium hydroxide (KOH) in an alcohol. The preferred solvent is 2-hexanol. The reaction may be performed at reflux initially at a temperature equivalent to the boiling point of the solvent, about 136° C. The products present at the end of this reaction may be isolated by distillation. Alternatively, the halocarbons produced in step 2 may be converted into dialkyl ethers.

Alkenes produced in the third step of the process may be converted into alkanes prior to isolation. This may be accomplished by a hydrogenation reaction performed using a platinum group metal catalyst (e.g., Pd, Pt, Rh, Ru, or Ir) in an atmosphere of $H_2$.

BRIEF DESCRIPTION OF CHART 1 AND FIGS. 1 AND 2

Chart 1: Reaction Pathway for Converting Polymers to Fuels. Chart 1 is a diagrammatic representation of the overall reaction pathway in which cellulose or hemicellulose is converted into hydrocarbon fuels. The polymeric starting material may be derived from biomass and need not be in a dry form. For purposes of simplicity, the diagram only shows the reaction products produced using cellulose as the starting material.

FIG. 1: Conversion of Polyhydric Alcohols into Halocarbons and Hydrocarbons (Total Ion Chromatogram of Reaction Products). Polyhydric alcohols are reacted with various concentrations of hydrogen iodide and reducing agent (preferably phosphorous acid or hypophosphorous acid) and the resulting products are analyzed by gas chromatography/mass spectrometry. An example of the results obtained (in this case using sorbitol as the polyhydric alcohol) is shown as FIG. 1.

FIG. 2: Conversion of Halocarbons to Alkenes (Total Ion Chromatogram of Reaction Products). Halocarbons produced from polyhydric alcohols (see Chart 1) are converted to alkenes by an elimination reaction performed using potassium hydroxide in a solvent of 2-hexanol. Products are analyzed by gas chromatography/mass spectrometry. An example of the results obtained is shown as FIG. 2. Notice the formation of large amounts of hexenes and the disappearance of $C_6H_{13}I$, $C_6H_{12}I_2$ etc.

DEFINITIONS

In order to provide a clear and consistent understanding of the specification and claims, including the scope to be given to the terms used therein, the following definitions are provided.

Chemical reaction: As used herein, the term "chemical reaction" refers to a reaction performed under the mild conditions usually employed for reactions in glass vessels.

Fermentation: As used herein, "fermentation" refers to any enzymatic transformation in which an organic substance, particularly a carbohydrate, is anaerobically decomposed to form products such as alcohols, acids and carbon dioxide.

Pyrolysis: As used herein, "pyrolysis" refers to a chemical decomposition brought about by the action of heat.

Biomass: As used herein, "biomass" refers to material derived from present day living organisms, including green plants, crops and trees.

DETAILED DESCRIPTION OF THE INVENTION

Figure 1:
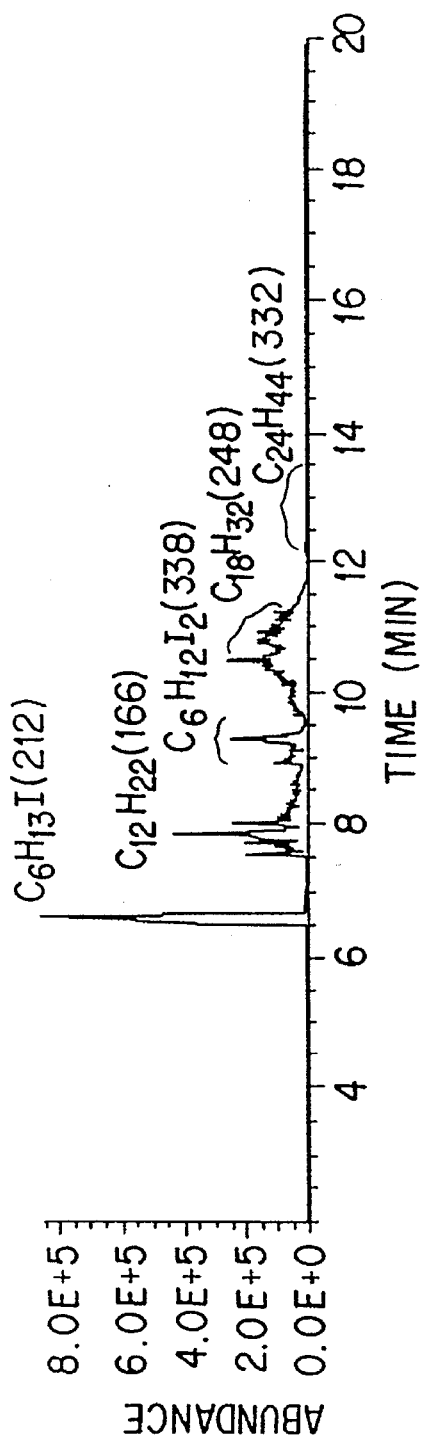

In the following description, reference will be made to various methodologies well-known to those skilled in the art of organic chemistry. Standard reference works setting forth general principles of organic chemistry include *Organic Chemistry* (T. W. G. Solomons, 5th ed., 1992) and *Advanced Organic Chemistry* (J. Mar., 3rd ed., 1985).

There are two main aspects to the invention disclosed herein. In its first aspect, the invention is directed to a novel method for converting polyhydric alcohols into iodoalkanes and hydrocarbons. Unlike similar reactions previously reported, the conversion is essentially quantitative and may be performed in aqueous solution under mild conditions.

In its second aspect, the invention is directed to a process in which cellulose or hemicellulose is converted into hydrocarbon fuels by a series of chemical steps. Each reaction in the pathway may be used directly on the products of the previous reaction.

I. Chemical Conversion of Polyhydric Alcohols to Hydrocarbons and Iodoalkanes

A unique chemical reaction has been developed for converting polyhydric alcohols into iodoalkanes and hydrocarbon fuels. The reaction is performed in aqueous solution containing polyhydric alcohol, hydriodic acid, and a liquid phase phosphorous-containing reducing agent. The reaction should be performed under an inert atmosphere, e.g., under an atmosphere of nitrogen or argon. Because the iodine formed as a by-product of the reaction is rapidly reduced to hydriodic acid by one or more phosphorous acids in one, homogeneous phase, an essentially quantitative yield of product may be obtained.

The preferred reducing agents are phosphorous acid and hypophosphorous acid. Ideally, sufficient reducing agent should be present to prevent $I_2$ from inducing phase separation and there should be sufficient HI to completely convert all of the polyhydric alcohol into iodoalklane and hydrocarbon. Examples of HI and reducing agent that are known to be effective are shown in Tables 1 and 2. The reaction may be carried out at a reflux temperature ranging from about 110° C. to about 127° C. under an inert atmosphere, e.g. an atmosphere of nitrogen.

Reaction products are immiscible with water and form an upper, nonaqueous layer that may be conveniently recovered either by simple decantation or by steam distillation. Unexpectedly, the reaction results in the simultaneous formation of low molecular weight hydrocarbon oligomers.

By adjusting the ratio of reagents and solvent, reactions can be performed in which about 99% of the product is in the form of iodoalkane (see Tables 1 and 2). Under other conditions, about 86–99% of the reaction product is recovered in the form of hydrocarbons (e.g., in reactions involving sorbitol, reaction products include isomers of $C_6H_{12}$, $C_{12}H_{22}$, $C_{12}H_{20}$, $C_{18}H_{32}$, $C_{18}H_{30}$, $C_{18}H_{28}$, $C_{24}H_{42}$ etc. that typically contain an alkene group and a ring). Iodocarbons detected are 2-iodohexane, isomers of $C_6H_{12}I_2$, and traces of $C_{12}H_{22}I_2$. These mixtures of iodocarbons and hydrocarbons may be conveniently phase-separated from the aqueous solution after 0.5 hours of reaction. Alternatively, they may be steam distilled from the reaction.

Hydrocarbon production is dependent, in large part, on the concentration of reactants. When the percentage of diluent (e.g. water) is low, the production of iodoalkanes is favored. More dilute mixtures favor the production of hydrocarbons. The optimum concentration of water for maximizing hydrocarbon production is about 48 percent. At water concentrations of greater than 50 percent, no reaction occurs.

Table 1 shows reactant concentration, reaction time and products of several representative reactions performed using sorbitol and mannitol as examples of six carbon polyhydric alcohols. Alternative $C_6$ polyhydric alcohols, e.g., dulcitol, should produce similar results. The mole percentages shown in Table 1 are expressed relative to moles of sorbitol, e.g. a mole ratio of 5 for HI means that there were 5 moles of HI for every one mole of sorbitol. The abbreviation R is used in the column headings to denote oligomeric groups and X indicates a halogen. R1 represents the combined percentage of all $C_6$ compounds that do not contain halogen such as hexene, hexadiene, 2,5-dimethyltetrahydofurans, hexanone, hexanol, and hexanal. R2 represents the percentage of $C_{12}$ hydrocarbons; R3 represents the percentage of $C_{18}$ hydrocarbons; and R4 represents the percentage of $C_{24}$ hydocarbons. RX represents the percentage of iodoalkanes and RX2 represents the percentage of diiodoalkanes. TX represents the total percentage of halocarbons, calculated as RX+RX2. TR represents the total percentage of hydrocarbons, calculated as R1+R2+R3+R4. % Y represents the yield calculated as TR+TX. M represents the method by which products were isolated where D denotes isolation by steam distillation and E denotes isolation by extraction. The abbreviation "tr" stands for "trace" and the abbreviation "hrs." stands for reaction time in hours. Numbers which appear in parentheses represent mole ratios that were calculated rather than experimentally measured.

TABLE 1

| | Mole Ratios | | | | | Product Yields % | | | | | | | | | |
|---|---|---|---|---|---|---|---|---|---|---|---|---|---|---|---|
| RXN# | HI | $H_3PO_3$ | $H_3PO_2$ | Other | hrs. | R1 | RX | R2 | RX2 | R3 | R4 | TX | TR | % Y | M |
| SORBITOL REACTIONS | | | | | | | | | | | | | | | |
| 1 | (5) | (2.5) | | | 20 | | 99 | | | | | 99 | 0 | 99 | D |
| 2 | 11 | 5 | | | 2 | 1 | 53 | 19 | 10 | 7 | | 64 | 27 | 91 | D |
| 3 | 11 | | 2.5 | | 20 | | 30 | 31 | 4 | 35 | | 34 | 66 | 100 | D |
| 4 | 11 | | 2.5 | | 1 | | 19 | 34 | 10 | 31 | | 29 | 65 | 94 | D |
| 5 | 11 | | 5 | | 20 | 5 | 9 | 51 | 1 | 24 | 1 | 10 | 81 | 91 | D |
| 6 | 11 | 5 | | $H_2O$, 40 | 20 | 2 | 10 | 20 | 2 | 28 | 21 | 12 | 71 | 83 | D |
| 7 | 11 | 5 | | | 20 | | 77 | 9 | 4 | tr | | 81 | 9 | 90 | E |
| 8 | 11 | 4 | | | 2 | 7 | 30 | 37 | 4 | 2 | | 34 | 46 | 80 | E |
| 9 | 11 | | 5 | | 27 | 1 | 20 | 48 | 4 | 19 | 1 | 24 | 69 | 93 | E |
| 10 | 7 | 7.5 | | | 20 | tr | 21 | 12 | 2 | 64 | 5 | 23 | 81 | 104 | E |
| 11 | 6 | 5 | | $P_2O_5$, 2.5 | 2 | 1 | 31 | 15 | 6 | 50 | | 37 | 66 | 103 | E |
| 12 | 11 | | 5 | $H_3PO_4$, 5 | 13 | 7 | 29 | 45 | 1 | 21 | | 30 | 73 | 103 | E |
| MANNITOL REACTIONS | | | | | | | | | | | | | | | |
| 13 | 11 | | 5 | | 2 | 8 | 9 | 34 | 4 | 24 | | 13 | 66 | 79 | E |

As shown in Table 2, reactions performed using xylitol as the starting polyhydric alcohol gave similar results. Products observed include pentene, pentanone, 2-iodopentane, and the $C_{10}$, $C_{15}$, and $C_{20}$ oligomers. Reaction #14 in Table 2 produced only halocarbons. Thus, the 33% in parentheses under the R2 column actually means R2X compounds.

TABLE 2

XYLITOL REACTIONS

| | Mole Ratios | | | | | Product Yields % | | | | | | | | | |
|---|---|---|---|---|---|---|---|---|---|---|---|---|---|---|---|
| RXN# | HI | $H_3PO_3$ | $H_3PO_2$ | $H_3PO_4$ | hrs | R1 | RX | R2 | RX2 | R3 | R4 | TX | TR | %Y | M |
| 14 | 5.2 | 4.4 | | | 1 | | 44 | (33) | 6 | | | 83 | 0 | 83 | D |
| 15 | 9 | 4 | | | 2 | 38 | 35 | | 8 | 9 | | 43 | 47 | 90 | E |
| 16 | 6 | 4.4 | | | 24 | | 1 | 12 | tr | 32 | 22 | 2 | 67 | 69 | E |
| 17 | 6 | | | 2.5 | 24 | | tr | 15 | tr | 24 | 4 | 1 | 43 | 44 | E |

The experimental procedure used for reaction #3 of Table 1 is representative of the conditions used in all of the reactions shown in both Table 1 and Table 2. D-Sorbitol (4.55 g, 25 mmol), colorless concentrated hydriodic acid (36.6 mL of 56.5% HI, 275 mmol), and hypophosphorous acid (6.5 mL of 50% $H_3PO_2$, 62.5 mmol) were refluxed (118° C.) under a nitrogen atmosphere for about 20 hours. At the end of this time, the reflux condenser was exchanged for a distillation head and the mixture steam distilled until no organic material was observed in the distillate. The distillate was then diluted with water and extracted with $CH_2Cl_2$. The acid mixture remaining in the reaction pot was also diluted with water and extracted with $CH_2Cl_2$. For convenience of analysis, both $CH_2Cl_2$ extracts were combined, dried over $Na_2SO_4$ and the solvent removed by rotary evaporator to give 3.582 g of product. Except for the conditions listed in the Tables, all of the other reactions were performed in an identical manner. Products were analyzed by GC/MS as discussed below.

In evaluating the results obtained from reactions, there are several points which should be borne in mind. First, the complete removal of the $CH_2Cl_2$ used to extract reaction products prior to analysis usually results in a substantial loss of hexene and a partial loss of RX. This may account for the low total yield reported for some of the sorbitol reactions in Table 1. In the case of reactions using xylitol as starting material, pentenes are lost in samples undergoing steam distillation due to their high volatility.

In order to avoid inaccuracies due to the loss of volatile reaction products, some reactions were not steam distilled before extraction but were simply cooled, diluted with water, and extracted. These "extracted only" reactions are designated with an "E" under the method (M) column in the tables (reactions where products were distilled are designated with a "D"). Water, $P_2O_5$ and concentrated phosphoric acid ($H_3PO_4$ 85%) were each added to several reactions during the study as denoted in the column marked "other" in Table 1.

Reaction products were analyzed by a Hewlett Packard 5890-II Gas Chromatograph close coupled to a HP-5988A Mass Spectrometer. A nonpolar capillary column (HP-1, 0.2 mm ID×12.5 m×0.33 μm film of crosslinked methyl silicone gum) was programmed to run for 1 minute at 26° C., to then increase in temperature at a rate of 5 degrees per minute for 3 minutes and then at a rate of 10 degrees per minute until the maximum temperature of 270° C. was reached. The column continued to run at the maximum temperature for a period of 5 minutes.

Using this procedure, several isomers of the general formulas shown in the tables were separated and identified by their mass spectra. The area percents of all identical mass isomers were summed in order to simplify calculations. The mole percent yields were calculated from these areas, as well as the molecular mass, and the stoichiometry. The total yield (% Y) for each reaction reported in Tables 1 and 2 is the sum of these group calculations. Small or trace amounts of hexene (three isomers), hexadienes, 2,5-dimethyltetrahydrofurans, hexanones, hexanols, and hexanal are occasionally found. All these are included in Table 1 under the column labeled R1 and are also included when determining the percentages reported in the total hydrocarbon column (TR). FIG. 1 shows an annotated Total Ion Chromatogram as an example of typical results obtained.

Hydrocarbons such as those reported in Tables 1 and 2 do not form when glucose is used as the starting material. Nor do such products form on treatment of wood with HI (Cooper, D. et. al., *Canadian Bioenergy R&D Semin. [Proc.]* 5th, pp. 455 (1984)). In fact, it is reported that $H_3PO_2$ greatly suppresses the yield of oil products from wood. Id.

II. Process for the Conversion of Cellulose or Hemicellulose to Hydrocarbon Fuels The present invention is also directed to a process for the conversion of cellulose, hemicellulose or mixtures of cellulose and hemicellulose to hydrocarbon fuels. The process comprises two to four separate reactions, two of which can be performed in water. In the first step, the cellulose (or hemicellulose) polymer is reductively depolymerized to form sorbitol (or xylitol). Reactions accomplishing such depolymerization are well known in the art (Sharkov, V. I., *Angew. Chem. I.E.E.* 2:405 (1963)).

In the second step of the process, the reaction products of step 1 are reduced to a mixture of iodocarbons (principally 2-iodohexane in the case of sorbitol and 2-iodopentane in the case of xylitol) and hydrocarbons using the hydriodic acid reaction described in section I above. This reaction takes place in boiling aqueous solution and is performed at atmospheric pressure. The reaction products are immiscible in water and may be simply removed by decantation or steam distillation. Unexpectedly, a highly controllable oligomerization reaction takes place simultaneously when reduction is carried out as described herein (see Tables 1 and 2 and associated discussion). Thus, step 2 of the claimed process not only provides an intermediate to $C_6$ hydrocarbons from the reduction of sorbitol, but also directly provides $C_{12}$, $C_{18}$ and $C_{24}$ hydrocarbons. These represent fuels in the range of gasoline, kerosene, diesel, and fuel oil, respectively.

Reaction conditions can be controlled so as to favor hydrocarbons of a desired mass. For example, reactions may be performed which favor the production of either the $C_6$ intermediate (and thus eventually $C_6$ hydrocarbons) (99%) or the $C_2$ and $C_{18}$ hydrocarbons (80%) (see Table 1). In the latter case, the remaining iodohexanes may be converted into hydrocarbons as described in step 3 below. Material balances (yields) are 100% (±4%). If the reaction is performed using xylitol, $C_5$ intermediates and $C_{10}$, $C_{15}$ and $C_{20}$ hydrocarbons are produced.

When mixtures of sorbitol and xylitol are reacted, $C_5$ and $C_6$ intermediates as well as $C_{11}$, $C_{12}$, $C_{17}$, $C_{18}$ etc. hydrocarbons are produced. Thus, it appears that with such mixture, $C_5$ molecules prefer to oligomerize with $C_6$ molecules and only traces of $C_{10}$ are found.

When reactions are performed for the purpose of producing fuels, it is desirable to include a third step in the process in which the halocarbons produced in step 2 are converted into either hexenes or pentenes. These alkenes may either be isolated by distillation or, alternatively, they may undergo an optional fourth reaction step in which they are reduced to alkanes.

Alternatively, the alkyl iodides produced in step 2 may be made into dialkyl ethers for use as fuel additives. Such oxygenates greatly reduce emissions while boosting octane rating. For example, $C_6I$ have been coupled to bis(2-hexyl) ether by a phase transfer type reaction as described in U.S. Pat. No. 3,914,320. When such a reaction is performed on a mixture of alkyl iodides and hydrocarbons from step 2, an oxygenated fuel blend is produced.

The individual reaction steps which comprise the claimed process are described below and may be seen in chart 1.

Step 1: Reductive Depolymerization of Biopolymers

In the first step of the claimed process, cellulose is converted to sorbitol in near quantitative yields, preferably by simultaneous hydrolysis and catalytic hydrogenation. Alternatively, hemicellulose may be converted into xylitol or mixtures of xylitol and sorbitol, depending upon its source. Methods for carrying out these depolymerization reactions are described in the literature and are suitable for use in the process (Sharkov, V. I., *Angew. Chem. I.E.E.* 2:405 (1963)).

In a preferred embodiment, depolymerization is accomplished by means of an acid catalyzed hydrolysis and, simultaneously, a catalytic hydrogenation (see e.g. chart 1, step 1). The reaction takes place in water containing 0.7% $H_3PO_4$ and 0.5% Ru/charcoal catalyst. It proceeds at a temperature of 165° C. for one hour and at an $H_2$ pressure of 600 psi (Sharkov, V. I., *Angew. Chem. I.E.E.* 2:405(1963)).

Step 2: Conversion of Polyhydric Alcohols into Iodoalkanes and Hydrocarbons

The method by which polyhydric alcohols are converted into iodoalkanes and hydrocarbons is described in detail in section I above. The expected reaction products when sorbitol is used in the reactions are shown in Table 1. The expected reaction products when xylitol is used in the reaction are shown in Table 2.

Step 3, Option 1: Conversion of Iodoalkanes to Alkenes.

The halocarbons found within the mixture of products produced by step 2 may be converted to alkenes. Preferably, the conversion is accomplished by an elimination reaction using potassium hydroxide (KOH) in a solvent of 2-hexanol. The reaction is performed at the reflux temperature of the solvent (about 136° C.). Alcohol solvent may be coproduced in this elimination reaction by a competing substitution mechanism.

The large difference in the boiling points of hexene (68° C.) and 2-hexanol (136° C.) from the other higher mass hydrocarbons (estimated to be about 210° C. for $C_{12}$ hydrocarbons and 300° C. for $C_{18}$ hydrocarbons), allows for a facile separation by distillation. The $C_{12}$ and $C_{18}$ alkene mixtures can either be separated by continued vacuum distillation or be directly used as fuel. Alternatively, the alkenes in the mixtures can be hydrogenated to alkanes in order to produce a fuel with different properties. Such a blend of isomers depresses the melting point of the fuel thereby helping it to remain liquid.

Figure 2:
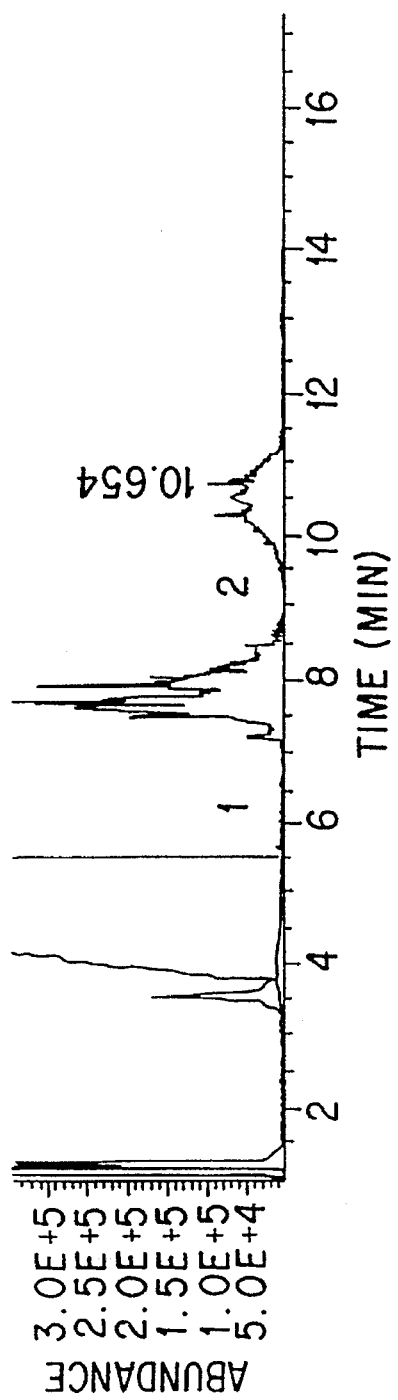

An annotated Total Ion Chromatogram is shown in FIG. 2 as an example of the results typically obtained from reaction step 3 of the claimed process. The results shown were obtained from an experiment in which a mixture of products from a step 2 reaction (2.075 g) was combined with powdered KOH (0.820 g) and 5 mL of 2-hexanol. The mixture was brought to reflux and maintained there for 10 minutes, during which time a large amount of KI precipitated from the reaction. FIG. 2 indicates that the procedure resulted in the complete reaction of all RI and $RI_2$.

Option 2: In an alternative third step, alkyl iodides produced in step 2 have been converted into dialkyl ethers, e.g., by the reaction described in U.S. Pat. No. 3,914,320. As described above, the dialkyl ethers may serve as fuel additives to reduce emissions and increase fuel octane rating.

Step 4: Reduction of Alkenes to Alkanes

As an optional fourth step in the claimed process, the alkenes produced in step 3 have been catalytically hydrogenated to yield mixtures of alkanes and alkyl substituted cycloalkanes. This reaction may be performed simultaneously with step 3 or subsequent to step 3. The large difference between the boiling point of hexane and dodecanes, etc., again facilitates the separation of each group of alkanes from the other groups and from the alcohol solvent used in step 3.

III. Advantages of the Inventions Disclosed Herein

The present invention may be viewed as comprising two closely related processes. The first process is a chemical reaction designed to convert polyhydric alcohols primarily into hydrocarbons along with a lesser amount of halocarbons. As should be apparent from the discussion above, this reaction offers a number of advantages over previously disclosed procedures: (1) The presence of a phosphorous reducing agent causes the iodine formed during the reaction to be rapidly converted back into HI. As a result, there is a nearly quantitative conversion of polyhydric alcohol to product. (2) The reaction may be carried out under mild conditions. (3) The reaction may be carried out in an aqueous solvent. Reaction products are insoluble in water and form a separate, upper layer. This allows for their isolation by simple decantation. (4) By altering the concentration of reagents, oligomer formation can be controlled so as to favor the production of hydrocarbons of a specific type.

The conversion of polyhydric alcohols into hydrocarbons and iodoalkanes as discussed above provides a key step in the second process of the present invention. The second process comprises an efficient multistep chemical pathway for the conversion of the principle components of biomass, cellulose and hemicellulose, into hydrocarbon fuels. There are several aspects of the process that make it highly attractive, particularly from an economic point of view: (1) The carbon chain remains intact throughout the reaction process. (2) Each reaction occurs under relatively mild conditions and gives a very high yield. (3) Each reaction is catalytic and a hydrogen or an electron is the only reagent consumed. (4) Initial reactions occur in an aqueous medium, which (5) allows the use of wet feedstocks available directly from the initial biomass separation. (6) Reactions either occur in $H_2O$ or in an alcohol produced as a by-product of the process. (7) Finally, a single pure product such as hexane or bis (2-hexyl) ether may be produced instead of the low yields of crude fuel mixtures that result from previously described methods.

The multistep process disclosed herein is capable of utilizing an inexpensive feedstock such as newspaper (69% hiolocellulose, $10 per ton). Wet cellulose as separated from raw biomass via steam explosion may be used directly without drying. The process should also be able to utilize wet feedstocks such as municipal sludge or aquatic plants.

IV. Uses of the Products of the Claimed Processes

Hexane, a low boiling point (68° C.) component of gasoline, has a good caloric value (19,400 BTU/lb) but a low Research Octane Number (RON=25). While most hexane is consumed in motor fuel, approximately $125 \times 10^6$ gallons are used as a solvent for oil seed extraction and as a medium for polymerizations (Dale, O. H., et. al., in *Kirk-Othmer Encyclopedia of Chemical Technology*, 3rd. ed., vol. 12, pp. 926 (1980)). Its synthesis from the process described herein should replace the prodigious fractional distillation and molecular sieve adsorption processes which are presently used for producing pure n-hexane suitable for use as a solvent.

Bulk solvent of 95% hexane comprised of several $C_6$ isomers currently sells for about $1.10 per gallon (FOB refinery), whereas a pharmaceutical grade costs over $6 per gallon. Derivation of a hexane mixture from crude oil causes its price to be about the same as the price of retail gasoline absent fuel taxes. However, solvents of greater than 99% n-hexane (one isomer) are currently available only in small quantities and have a retail price of about $151 per gallon (Aldrich Chemical Company Catalogue, Milwaukee, Wis., 1992-1993 edition). In contrast, hexene has a RON of 93, a density of 0.68, and an H/C ratio of two, all ideal for gasoline.

The $C_{12}$ hydrocarbons produced by the claimed process have several properties that make them desirable as fuels. Their low volatility, high degree of branching, cyclic structure, partial unsaturation and H/C ratio of 1.8 should contribute to a high RON. This group of hydrocarbons might be used as a narrow boiling point range gasoline. The $C_{12}H_{22}$ isomers might best be represented by 1,2,4-trimethyl-3-propylcyclohexene (MW=166) as shown in chart 1, however this structural assignment is tentative. Alternatively, estimation from other fuel data suggests that this $C_{12}$ mixture may have a density of 0.8 and a boiling point of about 210° C. and thus be similar to kerosene.

The $C_{18}$ and $C_{24}$ isomer mixtures produced by the claimed process are likely to have properties in the diesel and fuel oil ranges.

All references cited herein are fully incorporated by reference. Having now fully described the invention, it will be understood by those of skill in the art that the invention may be performed within a wide and equivalent range of conditions, parameters and the like, without affecting the spirit or scope of the invention or any embodiment thereof.

What is claimed is:

1. A method for reducing a polyhydric alcohol to an alkene, cyclic alkene, iodoalkane or a mixture thereof, comprising reacting said polyhydric alcohol with;
   a) hydriodic acid at a mole ratio of between about 5 and about 11 moles of said hydriodic acid per mole of said polyhydric alcohol; and
   b) either phosphorous acid or hypophosphorous acid at a mole ratio of between about 2.5 and about 7.5 moles of phosphorous acid or hypophosphorous acid per mole of said polyhydric alcohol;

wherein the reaction is performed:
   c) in an aqueous solution having a water content of less than 50%; and
   d) in an inert atmosphere.

2. The method of claim 1, wherein said polyhydric alcohol is reacted with phosphorous acid.

3. The method of claim 1, wherein said polyhydric alcohol is reacted with hypophosphorous acid.

4. The method of claim 1, wherein said polyhydric alcohol is sorbitol.

5. The method of claim 1, wherein said polyhydric alcohol is xylitol.

6. The method of claim 1 wherein said polyhydric alcohol is mannitol.

7. A process for converting cellulose or hemicellulose into a hydrocarbon fuel comprising the steps of:
   a) depolymerizing said cellulose or hemicellulose to form sorbitol or xylitol or a mixture thereof; and
   b) reacting the sorbitol or xylitol or mixture formed in step a) according to the method of claim 1, to form an iodoalkane and said hydrocarbon fuel.

8. The process of claim 7, further comprising:
   c) converting the iodoalkane formed in step b) to an alkene, wherein said alkene is either 2-hexene, or 2-pentene.

9. The process of claim 7, further comprising:
   c') converting the iodoalkane formed in step b) to a dialkyl ether.

10. The process of claim 8, further comprising:
    d) converting the alkene formed in step c) into ether pentene or hexane.

11. The process of any one of claims 7–10, wherein said sorbitol or xylitol is reacted with phosphorous acid.

12. The process of any one of claims 7–10, wherein said sorbitol or xylitol is reacted with hypophosphorous acid.

13. The process of any one of claims 7–10, wherein said depolymerization of the cellulose or hemicellulose in step a) is accomplished by performing a hydrolysis of said cellulose or hemicellulose in aqueous solution containing about 0.7% $H_3PO_4$ and about 0.5% ruthenium on a charcoal support, wherein said hydrolysis proceeds at a temperature of about 165° C. and at an $H_2$ pressure of about 600 psi.

14. The process of either claim 8 or 10, wherein the conversion of said iodoalkane to said 2-hexane or 2-pentene in step c) is accomplished by reacting the iodoalkane and hydrocarbon produced in step b) with potassium hydroxide in a solvent of 2-hexanol, wherein the reaction proceeds at reflux.

15. The process of claim 10, wherein the conversion of alkenes to alkanes in step d) is accomplished by hydrogenating said alkenes in the presence of a platinum catalyst under an atmosphere of $H_2$.

\* \* \* \* \*